United States Patent [19]
Bryan et al.

[11] Patent Number: 5,673,697
[45] Date of Patent: Oct. 7, 1997

[54] HIGH-RESOLUTION THREE, DIMENSIONAL ULTRASOUND IMAGING DEVICE

[75] Inventors: Thomas A. Bryan, Goleta; Brian E. Holtz, Santa Barbara; Gilbert F. Perleberg; Francis P. Diani, both of Goleta; George S. Hardie; James C. Robertson, both of Santa Barbara, all of Calif.

[73] Assignee: Raytheon Company, Lexington, Mass.

[21] Appl. No.: 637,162

[22] Filed: Apr. 24, 1996

(Under 37 CFR 1.47)

[51] Int. Cl.$^6$ .................................................... A61B 8/00
[52] U.S. Cl. ........................ 128/660.07; 128/916; 73/626
[58] Field of Search ..................... 128/660.07, 660.08, 128/660.09, 661.01, 661.02, 661.1, 916; 73/618, 625, 626; 367/138, 7

[56] References Cited

U.S. PATENT DOCUMENTS

| | | |
|---|---|---|
| 4,279,157 | 7/1981 | Schomberg et al. . |
| 4,338,948 | 7/1982 | Perez-Mendez et al. . |
| 4,395,909 | 8/1983 | Steiberg et al. . |
| 4,495,816 | 1/1985 | Schlumberger . |
| 4,625,555 | 12/1986 | Fujii . |
| 4,669,311 | 6/1987 | McKinnon . |
| 4,899,318 | 2/1990 | Schlumberger et al. . |
| 5,305,752 | 4/1994 | Spivey et al. . |
| 5,417,218 | 5/1995 | Spivey et al. . |
| 5,581,517 | 12/1996 | Gee et al. ............................... 367/138 |

OTHER PUBLICATIONS

Havlice, James and Taenzer, Jon C. "*Medical Ultrasonic Imaging: An Overview of Principles and Instrumentation*", Reprinted from Proc. IEEE, vol. 67, pp. 620–641, Apr. 1979.

Dines, Kris and Lytle, Jeffrey "*Computerized Geophysical Tomography*", Reprinted from Proc. IEEE, vol. 67, pp. 1065–6073, Jul. 1979.

Lu, J.-Y and Greenleaf, J.F. "*Pulse–Echo Imaging Using a Nondiffracting Beam Transducer*", Ultrasound in Med. & Biol., vol. 17, No. 3, pp. 265–281, 1991.

Zhu, Qing and Steinberg, Bernard "*Large Transducer Measurements of Wavefront Distortion in the Female Breast*", Ultrasonic Imaging, vol. 14, pp. 276–299, 1992.

Steinberg, Bernard "*A Discussion of Two Wavefront Aberration Correction Procedures*", Ultrasonic Imaging, Apr. 1992.

*Primary Examiner*—George Manuel
*Attorney, Agent, or Firm*—Michaelson & Wallace

[57] ABSTRACT

An acoustic imaging device for providing an image of a body in a medium, includes a plurality of acoustic transmit elements and a plurality of acoustic receive elements, an apparatus for activating one of the transmit elements to generate an ultrasonic signal, an apparatus to selectively receive and record from each of the receive elements a set of data representing a phase, amplitude and transit time of the ultrasonic signal, a first computing apparatus for calculating a velocity map of propagation velocity values in each of a plurality of volume elements including the body and the medium using the data set, and a second computing apparatus for calculating a reflectance map, including a coherent sum of reflectance values at selected points in the plurality of volume elements using the data set.

10 Claims, 2 Drawing Sheets

HIGH-RESOLUTION THREE, DIMENSIONAL ULTRASOUND IMAGING DEVICE

BACKGROUND OF THE INVENTION

1. Technical Field

The present invention relates to a device and method to form high resolution images of objects by measuring the transmission and reflection of ultrasound beams from the object in three-dimensions.

2. Background Art

It is known in the art to use ultrasound measurements to produce two-dimensional images of objects that cannot be observed with optical means, such as images of interior portions of the human body. Although phased-array transmitters are used to form sound beams, the return signal is not integrated coherently and no correction is made for differences in the sound propagation velocity as it propagates through an inhomogeneous medium. Uncorrected variances in the propagation velocity cause image blurring. Further, an inability to detect weak signals contributes to a lower resolution image.

It is an object of the invention to produce three-dimensional images of objects using measurements of transmitted and reflected acoustic energy. It is another object of the invention to produce higher-resolution images than are available with current ultrasound imaging techniques. It is another object of the invention to correct for velocity variances in the medium in which the object is suspended and the object to be imaged. It is a further object of the invention to improve the reception of reflected ultrasound signals by comparing the phase of reflected signal to the transmitted signal using coherent reception.

SUMMARY OF THE INVENTION

An acoustic imaging device for providing an image of a body in a medium, including a plurality of acoustic transmit elements and a plurality of acoustic receive elements, an apparatus for activating one of the transmit elements to generate an ultrasonic signal, an apparatus to selectively receive and record from each of the receive elements a set of data representing a phase, amplitude and transit time of the ultrasonic signal, a first computing apparatus for calculating a velocity map of propagation velocity values in each of a plurality of volume elements including the body and the medium using the data set, and a second computing apparatus for calculating a reflectance map, including a coherent sum of reflectance values at selected points in the plurality of volume elements using the data set.

DETAILED DESCRIPTION OF THE PREFERRED EMBODIMENT

Figure 1:
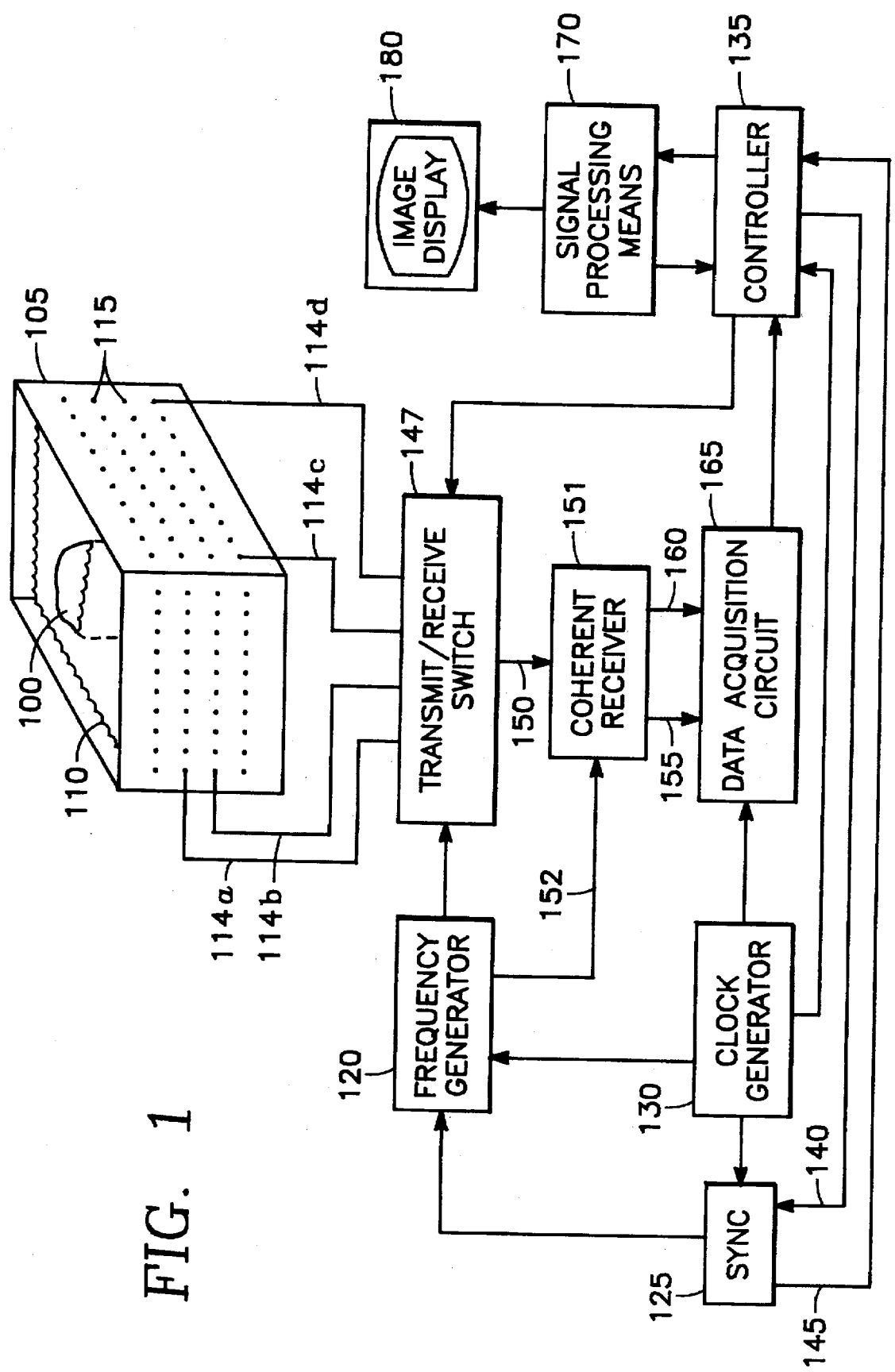
FIG. 1 is a block diagram of an imaging system according to the invention.

An object 100 is suspended in a chamber 105 filled with an acoustic transmitting medium 110, such as water. A plurality of acoustic transducers 115 are mounted on five sides of the chamber 105. Although a higher number of transducers 115 will increase resolution of the image generated, one embodiment of the invention used 600 transducers 115 spaced at approximately 0.100 inches apart on five sides of a chamber 105 including a cube having sides of two inches in length. The top of the chamber 105 was left open for access by the object 100. In deciding a number of transducers 115, factors such as the costs of equipment and data processing would be balanced against the higher resolution achievable with more transducers.

One preferred embodiment of the transducers 115 is formed by placing a plurality of wires, for example 30 gauge copper, in contact with a sheet of piezoelectric material, for example PZT, at each place that a transducer 115 is desired. A sheet of a corrosion resistant conductor, such as gold, is placed at zero electric potential and placed in contact with the piezoelectric material on the opposite side of the plurality of wires. When an electric potential is applied to one of the wires, a mechanical distortion or strain is produced in the piezoelectric material and an acoustic signal is transmitted into the medium 110. Conversely, when a mechanical stress such as an ultrasonic signal impacts the conductor surface, an electric potential is produced in the piezoelectric material, which is transmitted to the wire as a received ultrasonic signal.

The transducers 115 are energized by means of an ultrasonic signal provided by a frequency generator 120. The signal duration, or pulse window, is provided by a synchronizer 125. To ensure synchronous timing for the signals produced by both the frequency generator 120 and synchronizer 125, a clock generator 130 provides a timing signal at the desired frequency, for example at a conventional ultrasonic frequency of between 1 and 5 MHz.

Control of the transmitting function is provided by a digital controller 135, which cooperates with the synchronizer 125 in a "hand-shake" mode. For example, while the controller 135 is collecting (i.e. sampling) received signals, it sends a "busy signal" 140 to the synchronizer 125 that responds by not sending any pulse signals to the frequency generator 120. When the controller 135 completes a cycle of data collection, the busy signal 140 ceases and the synchronizer 125 sends a "sample signal" 145 to the controller 135 indicating a sample window in which to collect data from a received signal after the transmission of a pulse is completed.

The controller 135 also controls the receive function of the system by sending a serial data signal to a switch 147, which signal configures the switch by connecting a selected one of transducers 115 to the frequency generator. The switch 147 has connections to each transducer 115 by means of lead lines 114A, 114B, 114C, 114D etc. The switch 147 sequentially samples each of the nontransmitting transducers to produce a received signal 150 and connects it to a coherent receiver 151. Coherent reception is well known in radar applications as a method to improve signal reception and reduce loss, and may be referred to as moving target indication ("MTI") signal processing (see M. Skolnik, "Introduction to Radar Systems", 1980, pp 119–121). Using a coherent reference signal 152, or "coho" signal, provided by the frequency generator 120, the coherent receiver 151 provides a an in-phase component 155 and quadrature component 160 of the received signal 150.

A data acquisition circuit 165 samples the components 155 and 160 at a rate at least equal to twice the bandwidth under the well-known Nyquist criterion. For example, a typical bandwidth for a system of the invention is 1 MHz and the sampling rate is at least 2 MHz, which sampling rate signal is provided by the clock generator 130. The circuit 165 also converts the analog components 155 and 160 to digital signals ("A/D conversion") and stores them during a receive cycle, i.e., during collection of signals from all of the transducers 115 that are not transmitting.

The controller 135 receives a stream of digital data from the circuit 165 representing the pulses received from each of the transducers 115 that are not transmitting. These receive signals are provided to a signal processing means 170, which may also sample the controller 135 for additional information, such as the timing and duration of the transmit signal. After processing the signals as described below, the signal processing means 170 provides image data to an image display 180.

The imaging process begins by insertion of the object 100 into the chamber 105 and filling it with the medium 110, such as water. Measurements are taken by exciting a single transducer 115 with a sinusoidal acoustic pulse and sampling the time records of the components 155 and 160 at each of the other transducers 115. This process is repeated for each of the other transducers 115 in the chamber 105. These time records were then analyzed to produce an image of the object 100, as described below.

A first step in the process was to compute the propagation velocity over a three-dimensional grid in the chamber 105, which was referred to as a velocity map. The method used is referred to as axial tomography, which is used in geophysics to produce velocity profiles in soil (K. Dines and R. Lytle, "Computerized Geophysical Tomography", Proc IEEE, Vol 67, pp. 1065–1073, 1979). A straight line ray optics model for energy propagation between sensors is used and the velocity is calculated from line integrals along rays in the plane between pairs of transducers 115.

Figure 2:
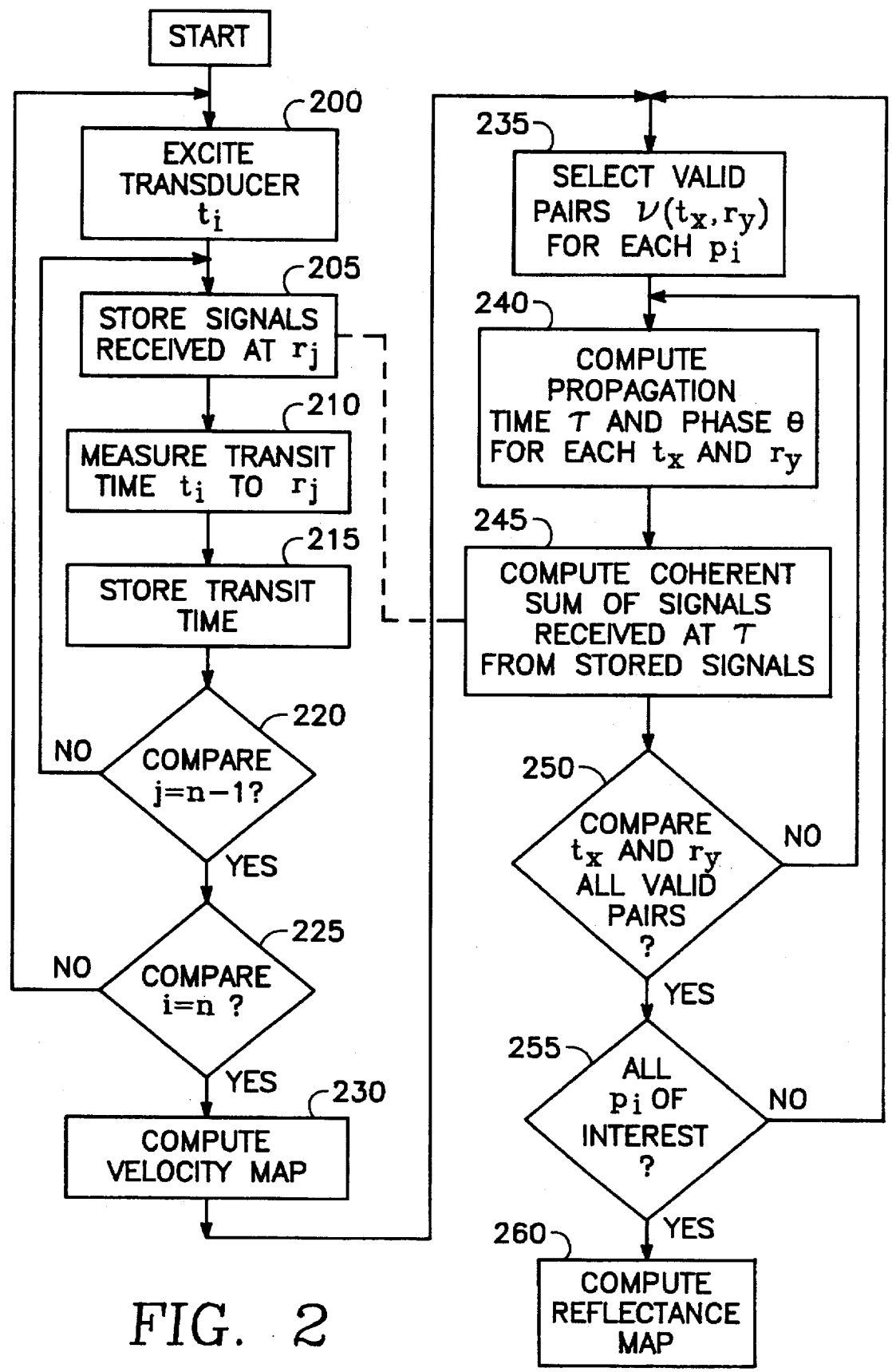
FIG. 2 is a flow diagram of the steps of a process according to the invention.

As shown in FIG. 2, the process begins by exciting a selected transducer, i.e. a transmitting transducer $t_i$, (Block 200) and storing the signals received at each of the other transducers that are not transmitting, i.e., receiving transducers $r_j$ (Block 205). In discrete terms, for each transducer 115 (FIG. 1) a time record of pulses received at all other transducers 115 was recorded, which produced n-1 time records for each transducer, where n is the number of transducers. For all transducers 115, this resulted in n(n-1)/2 pulse records, to avoid counting records twice along an identical path.

To compute distance along a ray, the chamber is divided into an arbitrary number of volume elements, or voxels, which number is less than the number of pulse time records. This ensures that there are more linear equations produced, i.e., equations of motion along rays, than unknown quantities, i.e., propagation velocities in each voxel. The next step is to compute, for each ray between a pair of selected transmit and receive transducers 115, a distance covered by the ray in each voxel, and the sum of these voxel segments is the length of the ray.

Returning to FIG. 2, a transit time for an acoustic pulse along the rays connecting $t_i$ and each $r_j$ is computed (Block 210) using the method referred to previously as coherent reception to improve the detection and measurement of the magnitude of received signals. At each time interval determined by the sampling rate of the A/D conversion of the circuit 165, a square root of the sum of the squares of components 155 and 160 is computed to produce a received signal E. For example, an A/D conversion sampling rate of 2 MHz would result in a time interval of $5 \times 10^{-7}$ seconds. The time interval at which the received signal E starts to increase is a leading edge of the acoustic signal arriving at a receiving transducer $r_j$, and defines a time for the acoustic signal to transit the selected ray. The set of arrival times is then stored (Block 215).

The steps 205 through 215 are repeated for each receiving transducer $r_j$, or until n-1 signal and time records are measured and stored for each transmitting transducer (Block 220). A second transducer is then excited and n-1 signal and time records are measured and stored (Block 225). After this data is collected, a series of linear equations are solved as explained below using the time and distance data from the measurement phase of the process.

Using the equation of motion for the acoustic signal along a ray, the arrival time of an acoustic signal at a transducer can be represented as $$T = s_1 \left( \frac{t_1}{s_1} \right) + s_2 \left( \frac{t_2}{s_2} \right) + \ldots s_i \left( \frac{t_i}{s_i} \right)$$

where $s_i$ is the distance along the ray in each voxel traversed by the ray, $t_i$ is the transit time in each voxel and T is the transit time along over the ray. This can be expressed as the following line integral:

$$T = \int_R \frac{1}{v(x,y,z)} \, ds$$

where R is the path from the transducer to the receiver, and v (x,y,z) is the propagation velocity at point (x,y,z).

The series of linear equations to be solved on a computer (Block 230) can be expressed as $$T_i = \sum_{j=1}^{N} \frac{s_{ij}}{v_j} = \sum_{j=1}^{N} s_{ij} x_j$$

where $s_{ij}$ is the distance in voxel j for path i, $v_j$ is the average propagation velocity of voxel j, T is the total time of flight for path i, N is the number of voxels and $x_j = 1/v_j$ is defined as the "slowness" of voxel j. If M is the number of raypaths, this equation can be expressed in matrix form as the following $$\begin{bmatrix} S_{11} & S_{12} & \ldots & S_{1N} \\ S_{12} & S_{22} & \ldots & S_{2n} \\ \cdot & \cdot & & \cdot \\ \cdot & \cdot & & \cdot \\ \cdot & \cdot & & \cdot \\ S_{M1} & S_{M2} & \ldots & S_{MN} \end{bmatrix} \begin{bmatrix} x_1 \\ x_2 \\ \cdot \\ \cdot \\ \cdot \\ x_N \end{bmatrix} = \begin{bmatrix} T_1 \\ T_2 \\ \cdot \\ \cdot \\ \cdot \\ T_M \end{bmatrix}$$

$$\underbrace{\phantom{XXXXXXXXXX}}_{\text{Call this matrix } A} \underbrace{\phantom{XXX}}_{\text{Vector } x} \underbrace{\phantom{XXX}}_{\text{Vector } b}$$

This equation can also be written as Ax=b.

The elements of matrix A and vector b are known measured values and the elements of vector x are unknown. Further, matrix A has more rows than columns (i.e., M>N). Solving for x is a classic least squares problem and can be solved in a variety of ways. For example, one method that may be used is the sparse QR method because most of the elements of matrix A are zero (Matstoms, "Sparse QR Factorization in MATLAB", ACM Transactions on Mathematical Software, Vol. 20, No. 1, March 1994, pp. 136–159). However, brute force normal equations can also be used as follows $$x = (A^T A)^{-1} A^T b$$

After solving for x, $v_j$ may be derived as follows $$x = \begin{bmatrix} x_1 \\ x_2 \\ \cdot \\ \cdot \\ x_N \end{bmatrix} \text{ so that } \begin{matrix} v_1 = 1/x_1 \\ v_2 = 1/x_2 \\ \cdot \\ \cdot \\ v_N = 1/x_N \end{matrix}$$

The result of this process is a three-dimensional grid, or velocity map, of the propagation velocities for acoustic signals in each voxel of the chamber 105 (FIG. 1). The primary reason for computing the map is to correct for the variances in the velocities through the medium to allow for coherent integration in the reflectance map, which is the next step in the process of the invention.

A reflectance map is the calculated sum of energy reflected from all spatial points p=x,y,z in a region of interest, which is an arbitrarily chosen set of points in the chamber 105. Using the velocity map, the sound propagation time can be calculated between any point p in the chamber 105 and any transducer 115.

Returning to FIG. 2 (Block 235), for each point p there is selected a set of pairs of transmitting transducers $t_i$ and receiving transducers $r_j$ such that the angle formed by the point p, the transmitting transducer and receiving transducer is small enough to detect a signal transmitted directly between the transducers and one reflected at p. In other words, the energy would be considered reflected off the point p versus transmitted through the point. In a typical system of the invention, the angle necessary to satisfy this criteria is generally 90 degrees or less. In addition, if the transducers $t_i$ and $r_j$ are not omnidirectional, the pairs must be selected such that the point p is in the-main beam of each pair, e.g., within 60 degrees of a normal to each transducer. The set of pairs of transducers 115 selected in this manner is referred to a set of "valid pairs of transducers" $\sigma_p$ for point p.

For each point p in the region of interest, and for each pair of transducers $v_{ij} = (t_i, r_j)$ in the set of $\sigma_p$, the propagation time $\tau_{ipj}$ from the transmit transducer $t_i$ to the point p to the receive transducer $r_j$ is computed from the distance along the reflected ray and the velocity map (Block 240). Then, a cumulative sum of the signals E received at these times $\tau_{ipj}$ is made (Block 245) from the signal and time records generated during the measurement phase of the process (Block 205). For each point p, the steps 240 and 245 are completed for all pairs $v = (t_i, r_j)$ in the set of $\sigma_p$ (Block 250). This process is repeated for each point in the region of interest (Block 255), which may be selected to be a small portion of the chamber 105 (FIG. 1) with a large number of points in order to provide a high resolution image, or a large portion of the chamber 105 with a smaller number of points to provide a lower resolution image.

The total sum of energy for point p over all $\sigma_p$ is called the reflectance value for the point p and the set of reflectance values over all points in the region of interest is called the reflectance map (Block 260), which represents the reconstructed image of the object 100 (FIG. 1). Since the number and location of points p are chosen arbitrarily, the resolution of the reflectance map can be made fine or coarse.

The detection of the signals reflected off a point p is enhanced by using the technique of coherent integration to cancel out undesired reflected signals and increase the signal-to-noise ratio. Coherent integration is known in radar applications (see e.g. F. Nathanson, "Radar Design Principles", 1969, pp. 69–70) and is based on the observation that when sinusoidal signals with the same phase are summed, they complement one another. For example, if n in-phase signals are summed, each of amplitude A, than the summed signal will have amplitude nA.

However, if signals have phases that are uniformly distributed over the interval $[0,2\pi]$, then the expected value of a series of such signals will approach 0. In other words, if the signals are represented by $$S_i(t) = A_i(t) \sin(wt + \Theta_i)$$

where $\Theta_i$ is a random variable uniformly distributed over $[0,2\pi]$, then $$E[s_i(t)] = \lim_{n \to \infty} \frac{1}{n} \sum_{i=1}^{n} s_i(t) = 0$$

For each point p whose reflectance is to be computed (i.e. in the region of interest), the phase e is calculated at each receiver $r_j$ of the signal contribution from each frequency generator $t_i$ reflected off the point p, using $\tau_{ipj}$ (the propagation time from $t_i$ to p to $r_j$) and the frequency f of the signal, which calculation is expressed by $$\Theta_{ipj} = 2\pi f \tau_{ipj}$$

If we define all the in-phase components 155 and quadrature components 160 (FIG. 1) stored for transmitter i and receiver j, as $I_{ij}(t)$ and $Q_{ij}(t)$, and adjust the signal by forming the in-phase and quadrature components into a "complex signal" $S_{ij}(t)$, as follows:

$$S_{ij}(t) = I_{ij}(t) + i\, Q_{ij}(t).$$

This signal is then multiplied by $e^{-i\Theta}ipj$ to bring all the signals in to phase at point p. Then a sum of such signals over all i and j is made to obtain a reflectance value for p, expressed as:

$$r_p = \sum_{i,j} e^{-i\Theta ipj} S_{ij}(\tau_{ipj})$$

This value is a "coherent sum" (also known as a coherent integration or "sum in phase") for signals reflected off of point p. All other signal contributions from any other reflections (i.e. other than from point p) will not be summed in phase. Their phases will continue to be random and, consequently, their contributions will sum to approximately 0. Signals reflected off of point p will sum in phase, so their contributions will be magnified.

For example, if a point p is not a reflector, the amplitude of the coherent signal contributions will be approximately 0. However, if a point p is a reflector, then the amplitude of the reflectance value $r_p$ will be greater than 0, and will be large if point p is very reflective.

Although the present invention has been described with reference to preferred embodiments, workers skilled in the art will recognize that changes may be made in form and detail without departing from the spirit and scope of the invention.

What is claimed:

1. An acoustic imaging device for providing an image of a body in a medium, comprising:

a plurality of acoustic transmit elements and a plurality of acoustic receive elements;

means for activating one of said transmit elements to generate an ultrasonic signal;

means to selectively receive and record from each of said receive elements a set of data representing a phase, amplitude and transit time of said ultrasonic signal;

a first computing means for calculating a velocity map of propagation velocity values in each of a plurality of volume elements comprising said body and said medium using said data set;

a second computing means for calculating a reflectance map comprising a coherent sum of reflectance values at selected points in said plurality of volume elements using said data set.

2. The acoustic imaging device of claim 1 wherein said first computing means comprises:

a computer having stored in a memory, in respect of each said transmit element and each said receive element, a set of distances in each of said volume elements, along a ray connecting said transmit and receive elements, and said transit times, said computer being programmed for calculating propagation velocities in each of said volume elements.

3. The acoustic imaging device of claim 2 wherein said second computing means comprises:

said computer having stored in said memory said velocity map, said computer being further programmed for selecting sets of valid pairs of said transmit and said receive elements for points of interest, and for computing propagation times and phases for ultrasonic signals connecting said points of interest and said valid pairs, and for computing coherent sums of reflectance values for said points of interest.

4. The acoustic imaging device of claim 1 wherein said plurality of acoustic transmit elements comprises the same plurality of transducers comprised in said plurality of acoustic receive elements.

5. The acoustic imaging device of claim 4 wherein said plurality of transducers are comprised of a piezoelectric film.

6. The acoustic imaging device of claim 4 wherein said plurality of transducers are comprised of a piezoelectric composite.

7. The acoustic imaging device of claim 1 wherein said activating means comprises:

a switch having plural input nodes and plural output nodes, plural ones of which are connected to said plurality of acoustic transmit elements and acoustic receive elements;

a frequency generator connected to one of said input nodes of said switch and having plural input nodes;

a sychronizer for controlling a pulse duration of said ultrasonic signal and connected to one of said input nodes of said generator and plural input and output nodes;

a controller connected to an input and output node of said sychronizer for turning on said ultrasonic signal, and connected to another one of said input nodes of said switch for selecting one of said acoustic transmit elements for connection to said signal;

a clock connected to another of said input nodes of said generator, another input node of said sychronizer, and said controller.

8. The acoustic imaging device of claim 1 wherein said selective reception and recording means comprises:

a switch having plural input nodes and plural output nodes, plural ones of which are connected to said plurality of acoustic transmit elements and acoustic receive elements;

a coherent receiver connected to one of said output nodes of said switch for receiving said ultrasonic signal and said frequency generator for receiving a coherent reference signal, and having plural output nodes;

a data acquisition circuit connected to said output nodes of said coherent receiver for converting said ultrasonic signals to digital signals and storing said digital signals and having input nodes and an output node;

a controller connected to said output node of said data acquisition circuit for sensing and storing received signals, and connected to another one of said input nodes of said switch for selecting said acoustic receive elements for connection to said coherent receiver, and having an output connected to said first computing means and an input node;

a clock connected to another of said input nodes of said data acquisition circuit and said node of said controller.

9. The acoustic imaging device of claim 1 wherein said medium comprises water.

10. A method for providing an image of a body in a medium comprising the steps of immersing the body in the medium;

transmitting an ultrasonic signal from one of a plurality of acoustic transmit elements;

sensing a set of data comprising a phase, amplitude and transit time of the ultrasonic signal at each of a plurality of acoustic receive elements; and calculating a velocity map of propagation velocity values in each of a plurality of volume elements comprising said body and said medium using said data set; and calculating a reflectance map comprising a coherent sum of reflectance values at selected points in said plurality of volume elements using said data set.

\* \* \* \* \*

UNITED STATES PATENT AND TRADEMARK OFFICE
CERTIFICATE OF CORRECTION

PATENT NO. : 5,673,697
DATED : October 7, 1997
INVENTOR(S) : Bryan et al.

It is certified that error appears in the above-identified patent and that said Letters Patent is hereby corrected as shown below:

In Column 5, line 36, please change "$\sigma$" to --$\vartheta$--.

In Column 5, line 39, please change "$\sigma$" to --$\vartheta$--.

In Column 5, line 47, please change "$\sigma$" to --$\vartheta$--.

In Column 5, line 54, please change "$\sigma$" to --$\vartheta$--.

Signed and Sealed this

Third Day of March, 1998

Attest:

BRUCE LEHMAN

*Attesting Officer*     *Commissioner of Patents and Trademarks*